US006271438B1

(12) United States Patent
Logemann et al.

(10) Patent No.: US 6,271,438 B1
(45) **Date of Patent: *Aug. 7, 2001**

(54) TRANSGENIC PATHOGEN-RESISTANT PLANT

(76) Inventors: Jürgen Logemann, Lavendeltuin 5, NB Leiden (NL), 2317; Guido Jach, Maternusstrasse 22, Köln (DE), 50678; Birgit Görnhardt, Auf dem Knöpp 28, Köln (DE), 51145; John Mundy, NY Carlsberg Vej 6, 4th, V Copenhagen (DK), 1760; Jeff Schell, Carl-von-Linne-Weg 10, Köln (DE), 50829; Peter Eckes, Am Flachsland 18, Kelkheim (Taunus) (DE), 65779; Ilan Chet, Shikun Ezrachi, Nes Ziona (IL), 70400

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/138,873

(22) Filed: Aug. 24, 1998

Related U.S. Application Data

(62) Division of application No. 08/812,025, filed on Mar. 6, 1997, now Pat. No. 5,804,184, which is a division of application No. 08/457,797, filed on Jun. 1, 1995, now Pat. No. 5,689,045, which is a continuation of application No. 08/134,416, filed on Oct. 8, 1993, now abandoned.

(30) Foreign Application Priority Data

Oct. 9, 1992 (DE) ..... 42 34 131

(51) Int. Cl.[7] ..... A01H 1/06; A01H 5/00; C12N 15/00

(52) U.S. Cl. ..... 800/279; 800/301; 435/200; 435/209; 435/69.1; 435/320.1; 536/23.2; 424/94.61; 424/94.2; 514/12

(58) Field of Search ..... 800/279, 301; 424/94.61, 94.2; 514/12; 435/200, 209, 69.1, 320.1; 536/23.2

(56) References Cited

U.S. PATENT DOCUMENTS

| | | | |
|---|---|---|---|
| 4,940,840 * | 7/1990 | Suslow et al. | 800/205 |
| 4,970,168 | 11/1990 | Tumer | 435/317.1 |

FOREIGN PATENT DOCUMENTS

| | | |
|---|---|---|
| 163810286 | 3/1988 | (DE) . |
| 124040954 | 12/1990 | (DE) . |
| 440 304 * | 8/1991 | (EP) . |
| 148904371 | 5/1989 | (WO) . |
| 89119738 | 12/1991 | (WO) . |
| 69216632 | 10/1992 | (WO) . |
| 79217591 | 10/1992 | (WO) . |
| 19408009 | 4/1994 | (WO) . |

OTHER PUBLICATIONS

S. Wnendt et al., "Cloning and Nucleotide Sequence of a cDNA Encoding the Antifungal–Protein of *Aspergillus giganteus* and Preliminary Characterization of the Native Gene", Nuc. Acids Res. 18(13): 3987, Jul. 1990.*

R. Leah et al., "Biochemical and Molecular Characterization of Three Barley Seed Proteins with Antifungal Properties", J. Biol. Chem. 266(3): 1564–1573, Jan. 1991.*

Dunsmuir et al., Curr. Pl. Sci. and BioTech. in Agri., vol. 14, Adv. in Mol. Gen. of Plant–Microbe Interactions, Seattle Wash., Jul. 1992, Kluwer Acad. Publ. Netherlands, pp.567–571.

Bojsen et al., 1992, Dev. Plant Pathol. 2 (Mech. of Pl. Def. Res.) Symposium held Aug. 24–27, pp. 449.

Jach et al., 1992, Bio/Technol. 1:33–40.

Logemann et al., 1992, Bio/Technol. 10:305–308.

Broglie et al., 1991, Science 254:1194–1197.

Neuhaus et al., 1991, Plant Mol. Biol. 16:141–151.

Potrykus, 1990, Bio/Technology 8:535–542.

Leah and Mundy, 1989, Plant Mol. Biol. 12:673–682.

Legrand et al., 1987, Proc. Natl. Acad. Sci. U.S.A. 84:6750–6754.

Topfer et al., 1987, Nucl. Acids Res. 15:5890.

Hahlbrock and Grisebach, 1979, Ann. Rev. Plant. Physiol. 30:105–130.

Boller, 1985, Cellular and Molecular Biology of Plant Stress, UCLA Symposium, Mol. Cell. Biol. New Ser. 22:247–262.

* cited by examiner

*Primary Examiner*—Rebecca E. Prouty
(74) *Attorney, Agent, or Firm*—Baker Botts, LLP

(57) ABSTRACT

Transgenic pathogen-resistant organism whose genome contains at least two different genes under the control of active promoters with pathogen-inhibiting action. This organism is distinguished by a synergistic pathogen-inhibiting action. This action is evident particularly when the genes code for the gene products chitinese (ChiS, ChiG), glucanase (GluG), protein synthesis inhibitor (PSI) and antifungal protein (AFR).

13 Claims, 2 Drawing Sheets

TRANSGENIC PATHOGEN-RESISTANT PLANT

This application is a divisional of prior application No. 08/812,025 filed Mar. 6, 1997, now U.S. Pat. No. 5,804,184, which, in turn, is a divisional of prior application No. 08/457,797, filed Jun. 1, 1995, now U.S. Pat. No. 5,689,045, which is a continuation of prior application No. 08/134,416, filed Oct. 6, 1993, now abandoned.

FIELD OF THE INVENTION

The invention relates to a pathogen-resistant organism and to a process for generating it.

BACKGROUND OF THE INVENTION

It is known in the state of the art that infestation of a plant by pathogens causes a series of different reactions. These include, for example, changes in the cell wall structure, the synthesis of phytoalexins which have antimicrobial activity, the accumulation of so-called PR proteins (pathogenesis-related), protease inhibitors and enzymes with hydrolytic functions (Hahlbrock and Grisebach in Ann. Rev. Plant. Physiol., 30 (1979), 105–130).

Many pathogens (fungi and insects) have chitin as a constituent of their cell wall. By contrast, plants possess no chitin. It has now been demonstrated in some cases that there is enhanced production of chitinases in plants after infestation by pathogens. Chitinases are among the enzymes with hydrolytic functions and they catalyze chitin breakdown. It has now been possible to show that plants acquire an increased resistance to pathogens by the production of chitinases.

It is furthermore known to use a gene from barley plants whose gene product codes for an inhibitor of fungal protein synthesis. The incorporation of a corresponding inhibitor gene in transgenic plants led to improved resistance to fungi.

Finally, it has also been disclosed that the use of a polypeptide from Aspergillus giganteus is able to protect, by virtue of its antifungal activity, plants from infestation by fungi.

However, given this state of the art there is a need to provide further transgenic pathogen-resistant organisms. Moreover, the organisms which are particularly desired are those whose resistance is increased overall by comparison with the known organisms or is extended with respect to the number of possible pathogens.

This problem is solved by a transgenic pathogen-resistant organism having the features of the present invention.

The invention is based on the surprising finding that the incorporation of at least two different genes with pathogen-inhibiting action into the genome of an organism assists the latter to resistant pathogens to an extent going far beyond an additive effect of each of the genes on its own.

The dependent claims indicate further embodiments of the invention.

The genes can code for gene products which reduce the vitality of fungi. In particular, the genes can be of fungal, bacterial and plant, animal or viral origin. In particular, the gene products have properties which promote resistance to fungi. The gene products are chitinase (ChiS, ChiG), glucanase (GluG), protein synthesis inhibitor (PSI) and antifungal protein (AFP).

The transgenic pathogen-resistant organism can be a plant, and tobacco, potato, strawberry, corn, rape or tomato plants are preferred.

The invention also relates to DNA-transfer vectors with inserted DNA sequences as are indicated in detail in this description.

The invention furthermore relates to a process for the generation of pathogen-resistant organisms as are described herein, wherein at least 1 gene with pathogen-inhibiting action is transferred into the genome of an organism, and the pathogen-resistant organism is obtained (a) by crossing the organism with another, optionally transgenic, organism which contains at least one other gene with pathogen-inhibiting action, and subsequently selecting, and/or.

(b) by transformation of this other gene with pathogen-inhibiting action into the organism. The process can be used with DNA-transfer vectors with inserted DNA sequences corresponding to a gene with pathogen-inhibiting action as described herein.

Finally, the invention relates to a process for the generation of pathogen-resistant organisms, wherein vectors which comprise more than one gene with pathogen-inhibiting action are used for the transformation into the genome of an organism.

The invention also relates to a process for ensuring the resistance of organisms to pathogens, characterized in that the organism used is a transgenic pathogen-resistant organism according to the present invention or an organism whose genome contains at least one gene complying with the definitions used herein and at least one substance which is not expressed by the organism but corresponds to any other one of the gene products complying with the definitions given in this application is applied to the organism.

It was possible to achieve the synergistic effects very particularly with transgenic pathogen-resistant organisms to which the gene sequences which coded for proteins of the attached sequence listings A to E, or corresponded to the latter, were transferred or transfected. ChiS:

A DNA fragment is 1.8 Kb in size, that codes for a chitinase called ChiS (EQ ID NO:8) was isolated from the soil bacterium Serratia marcescens. In vitro investigations with purified ChiS protein sowed that it is able effectively to inhibit the growth of fungi, even in low concentrations. The reason for the inhibition is that the ChiS protein has a chitinase activity which is able to damage the tips of the fungal hyphae. In this way the fungus is unable to grow further and is inhibited. PSI:

The PSI gene originates from barley and codes for a protein which inhibits protein synthesis by fungi. In vitro tests show that even low concentrations of PSI are sufficient to inhibit various fungi such as, for example, Rhizoctonia solani.

AFP:

It is possible for a polypeptide which has antifungal activity to be isolated from the fermentation broth of Aspergillus giganteus and to be sequenced. This polypeptide is suitable as antifungal agent, for example as spraying agent and as preservative for industrial products and human and animal foods. It can furthermore be combined with other substances which have pesticidal activity, fertilizers or growth regulators. Inhibitory activities against fungi were detectable inter alia against various Aspergillus, Fusaria, Phytophthora and Trichlophyton species.

ChiG and GluG:

Two genes which code, respectively, for a chitinase (ChiG) and glucanase (GluG) can be isolated from certain types of barley. Purified ChiG protein or GluG protein inhibits various phytopathogenic fungi in virto (inter alia Rhizoctonia solani) (see R. Leah et al., Journal of Biological Chemistry, Vol. 266, No. 3 (1991), pages 1564–1573).

SUMMARY OF THE INVENTION

The inventors have now found, completely, surprisingly, that an at least binary combination of expression of PSI, AFP, ChiS, ChiG or GluG leads to synergistic effects in respect of the acquired resistance to fungi in transgenic plants. In particular, the effects of the individual substances in the combination are markedly exceeded. These include resistance to the fungus Rhizoctonia solani, Sclerotinia infestation, Botrytis infestation, etc.

Combinations according to the invention are (DNA and/or polypeptides):

(binary combinations)

ChiS, GluG; ChiS, PSI; ChiS, ChiG; ChiS, AFP; GluG, PSI; GluG, ChiG; luG, AFP; PSI, ChiG; PSI, AFP;

(ternary combinations)

ChiS, GluG, PSI; ChiS, GluG, ChiG; ChiS, GluG, AFP; GluG, PSI, ChiG; GluG, PSI, AFP; PSI, ChiG, AFP; ChiG, AFP, GluG (quaternary combinations) ChiS, GluG, PSI, AFP; ChiS, GluG, PSI, ChiG;

(quinary combination)

ChiS, GluG, PSI, AFP, ChiG

The invention furthermore relates to the combined use of the proteins with pathogen-inhibiting action, preferably ChiS, PSI, AFP, ChiG and GluG, against pathogens. Combined use also means in this context that at least a first pathogen-inhibiting substance is expressed by the organism and at least a second substance which has pathogen-inhibiting action is applied to the organism from outside.

The agents according to the invention also include those which contain the abovemented proteins in at least binary combination. The agents according to the invention can contain other active substances besides the proteins. The other active substances can be pesticides, fertilizers and/or growth regulators, and the agents according to the invention can be prepared in various formulations such as concentrates, emulsions, powders, formulations carriers, mixtures with other active substances, etc. The ChiS/PSI and AFP/PSI combination is particularly preferred. These proteins can be used particularly effectively to inhibit the growth of *Rhizoctonia solani,* especially in tobacco crops.

DETAILED DESCRIPTION OF THE INVENTION

Figure 1:
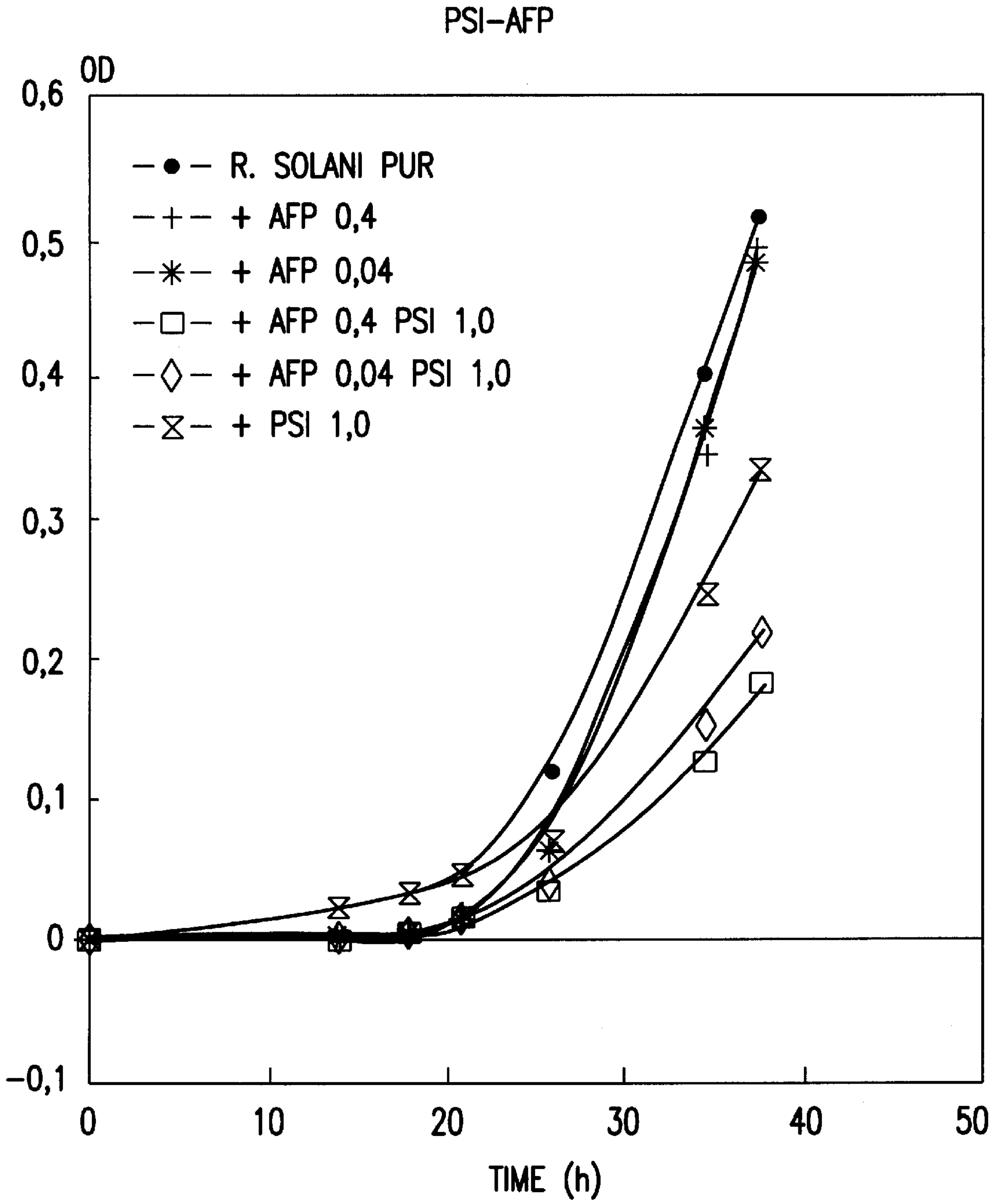
FIG. 1 shows the effects of AFP and PSA on *Rhizoctonia solani.*

The invention were relates to the use in a process according to the invention of a DNA sequence which codes at least for a polypeptide of sequences A to E in which sequence A is the sequence of a 60 amino acid AFP protein (SEQ ID NO:2); sequence A' is the sequence of a 51 amino acid protein (SEQ ID NO:3); sequence B is the sequence of the PSI protein (SEQ ID NO:5); sequence B' is the sequence of a protein encoded by an incomplete PSI-cDNA clone (SEQ ID NO:7); sequence D is the sequence of the ChiG protein (SEQ ID NO:10); and sequence E is the sequence of the GluG protein (SEQ ID NO:12), or to a pathogen-resistant organism, where its genome contains at least two different genes under the control of active promoters with pathogen-inhibiting action, where the genes are is each, case selected from the groups of sequences A to E in which sequence A is the sequence of a nucleic acid (SEQ ID NO:1) which comprises a region encoding AFP protein; sequence B is the sequence of a nucleic acid (SEQ ID NO:4) which comprises a region encoding PSI protein; sequence B' is the sequence of a nucleic acid (SEQ ID NO:6) which was identified as a portion of an incomplete PSI-cDNA clone; sequence C is the sequence of a nucleic acid (SEQ ID NO:8) encoding ChiS protein; sequence D is the sequence of a nucleic acid (SEQ ID NO:9) which comprises a region encoding ChiG protein; and sequence E is the sequence of a nucleic acid (SEQ ID NO:11) which comprises a region encoding GluG protein. The invention furthermore includes DNA sequences which hybridize with a DNA sequence which codes for polypeptides of amino-acid sequences A to E in which sequence A is the sequence of a 60 amino acid AFP protein (SEQ ID NO:2); sequence A' is the sequence of a 51 amino acid AFP protein (SEQ ID NO:3); sequence B is the sequence of a PSI protein (SEQ ID NO:5); sequence B' is the sequence of a protein encoded by an incomplete PSI-cDNA clone (SEQ ID NO:7); sequence D is the sequence of a ChiG protein (SEQ ID NO:10); and sequence E is the sequence of the GluG protein (SEQ ID NO:12), where these DNA sequences can be of natural, synthetic or semisynthetic origin and can be related to the abovementioned DNA sequence by mutations, nucleotide substitutions, nucleotide deletions, nucleotide insertions and inversions of nucleotide sequences, and for a polypeptide with pathogenic activity. The invention furthermore relates to a recombinant DNA molecule which contains at least one DNA sequence which accords with the preceding statements, where this DNA molecule can be in the form of a cloning or expression vector.

The invention relates to appropriate host organisms and intermediate hosts which are transformed with a recombinant DNA molecule which accords with the preceding statements. Preferred as intermediate host in the generation of a pathogen-resistant transgenic organism are strains of bacteria in particular so-called Agrobacteria strains.

The invention furthermore relates to the trangenic pathogen-resistant organisms obtained by the process according to the invention, in particular tobacco, potato, corn, pea, rape and tomato plants.

The DNA sequences according to the invention are, as a rule, transferred together with a promoter. Promoter sequences are recognized by the plant transcription apparatus and thus lead to constitutive expression of the gene associated with them in plants. The promoter, can, however. Also be pathogen-inducible and/or wound-inducible (WUN1) and/or tissue-specific and/or development-specific.

The genetic manipulation operations necessary for carrying out the invention, especially for expression of the gene in plants, are generally known. See for example the publication by Maniatis et al. in "Molecular cloning: A laboratory manual", Cold Spring Harbor (1982).

The invention is explained in detail in the following examples.

All the standard methods of molecular biology were carried out, unless otherwise indicated, as described by Maniatis et al. "Molecular cloning: a laboratory manual", Cold Spring Harbor (1982).

The DNA (SEQ ID NO:1; SEQ ID NO:4; SEQ ID NO;6; SEQ ID NO:8; SEQ ID NO:9; SEQ ID NO:11) coding for amino-acid sequences A to E (SEQ ID NO:2; SEQ ID NO:3; SEQ ID NO:5; SEQ ID NO:7; SEQ ID NO:10; SEQ ID NO:12), was initially cloned in a manner known per se and then transferred by conjugation into A. Tumefaciens LBA 4404 (A. Hoekema et al., Nature 303, 179–180). This took place by the method described by Van Haute et al. in EMBO J. 2, 411–418 (1983).

The transfer of DNA into that Agrobacterium was checked by isolating Agrobacterium DNA by the method described by Ebert et al. in Proc. Natl. Acad. Sci. USA 84 5745–5749 (1987). Restriction cleavage of the DNA, transfer to Hybond-N membrane (Amersham) and hybridization with a radioactively labeled DNA probe provided information about successful DNA transfer into the Agrobacterium.

The transformed Agrobacterium was then used to transform tobacco, rape, strawberry, tomato and potato plants.

The LBA4404 Agrobacteria required for the infection were initially cultivated in selective antibiotic medium (P. Zombrisky et al. in EMBO J., 1, 147–152 (1983)), sedimented by certification and washed in YEB medium without antibiotics (YEB=0.5% meat extract; 0.2% yeast extract; 0.5% peptone; 0.5% sucrose; 2 mM $MgSO_4$). After renewed sedimentation and taking up in $MgSO_4$ it was possible to use the bacteria for the infection.

The so-called leaf disk method was used for the infection.

Sterile leaves were used for the leaf disk infection. Leaf pieces about 1 cm in size are dipped in the previously described Agrobacteria suspension and subsequently transferred to 3MS medium (medium described by T. Murashige and F. Skoog in Physiol. Plant., 15, 473–497 (1962); 3MS=MS–3% sucrose). After incubation at 25° C. to 27° C. with 16 hours of light for two days, the leaf pieces were transferred to MSC16 medium (according to T. Murashige (see above); MSC16=MS+0.5 μg/ml HAP=0.1 μg/ml NAA+100 μg/ml kanamycin sulfate +500 μg/ml Claforan). Shoots appearing after 4–6 weeks were cut off and transplanted to MSC15 medium (according to Murashige (see above); MSC15=MS+2% sucrose, 500 μg/ml Claforan+100 μg/ml kanamycin sulfate). Shoots with root formation were analyzed further.

Monocotyledonous plants (including corn), but some dicotyledonous plants too, were transformed by direct gene transfer into protoplasts. These protoplasts were subsequently regenerated to intact plants (Example) J. Potrykus in Biotechnology 8 (1990), 535).

The resulting transgenic plants were infected with the fungus *Rhizoctonia solani* for testing purposes. For this purpose, fungal cultures were grown and thoroughly mixed in standard soil. This soil was then distributed in a dish and planted with the plants to be tested.

For the evaluation, each plant on a dish was assigned a value from 0 to 3. It was possible to calculate from this for each plant line an index which resulted from the sum of the values. The classification is as follows:

0=no symptoms (healthy)

1=slightly reduced size (compared with a non-infected control); no or very slight visible infestation 2=severe reduction in growth; severe symptoms of infestation 3=dead The rating is carried out in each case 14 days after the start of the series of tests.

EXAMPLE 1

Fungus inhibition test with combined proteins

The intention initially was to show that the proteins used here have synergistic effects in their combination. Fungal growth tests in vitro were carried out for this purpose.

These entailed a defined amount of *Rhizoctonia solani* fungal mycelium being mixed with 100 μl of potato dextrose solution and incubated in microtiter plates at 25° C. In this test there is a linear correlation between the growth of the fungus and the increase in the optical density at 405 nanometers. The inhibitory effect of proteins can be detected from a smaller increase in the optical density.

2–3 mycelium balls were taken from a liquid culture of R. Solani, mixed with 100 μl of KGB medium in an Eppendorf vessel and carefully homogenized with a glass mortar. This suspension was then mixed with 10 ml of KGB medium and passed through a sterile 100 μm screen. The optical density of this mycelium fragment suspension (100 μl aliquot) was adjusted to a value of 0.06–0.07 at 405 nanometers by adding medium. 100 μl samples were placed on a microtiter plate and mixed with the proteins to be tested. 7 parallels were measured per mixture. Mixtures which were mixed with the corresponding amounts of buffer served as controls. The plates were incubated in the dark at 25° C. for 48 hours, and the optical density of the cultures was measured at regular intervals.

Calculation of whether two proteins act together in an additive synergistic or antagonistic manner in the inhibition of fungal growth is possible from the measured data with the aid of the Colby formula which is described hereinafter and generally used (S. R. Colby in Wheeds, 15 (1967), 20–22).

To do this it was initially necessary to calculate the growth inhibition E to be expected theoretically with an additive behavior (the expected efficacy). This is given by:

$$E=W1+W2-((W1+W2)/100)$$

where W1 and W2 indicate the efficacies of the individual proteins, which is defined as that percentage deviation of the growth plot (in the presence of the protein) from the untreated control. The efficiency for a protein (at a defined time in the growth plot) is given by:

$$W1=(OD(K)-OD(P))/OD(K)\times 100 \text{ (percent)}$$

In this, OD(K) is the optical density of the untreated control and OD(P) is the optical density of the culture treated with the protein.

Thus, on combined use of two proteins, the following statements were possible: if the efficiency G measured in the experiment is identical to the expected value E, the behavior is additive. If, on the other hand, G is greater than E, the behavior is synergistic.

Using this test model, it emerged that the proteins ChiS, PSI, AFP, ChiG and GluG used in the Example surprisingly have synergistic inhibitory effects on various fungi, and these effects were achieved both by the combination of two types of protein and by multiple combination of the above-mentioned proteins.

For example, the following values were determined from the combination of ChiS and PSI protein and from the combination of AFP protein and PSI protein on the fungus *Rhizoctonia solani* (in each case two different ChiS and AFP concentrations with a constant RIP concentration):

ChiS+PSI:

The expected values were: E1=29.9%and E2=44.5%

The measured values were: G1=60.4%and G2=64.1%

The proteins ChiS and PSI therefore act together in a synergistic manner in the inhibition of the growth of R. Solani.

FIG. 1 shows the results obtained with the combination of the proteins and with the individual substances. According to the Figure, various ChiS concentrations (0.5 $\mu$g/ml and 0.05 $\mu$g/ml) are combined with PSI protein (1.0 $\mu$g/ml).

AFP+PSI:

The expected values were: E1=39.9% and E2=41.9%

The measured values were: G1=57.7% and G2=65.4%

Figure 2:
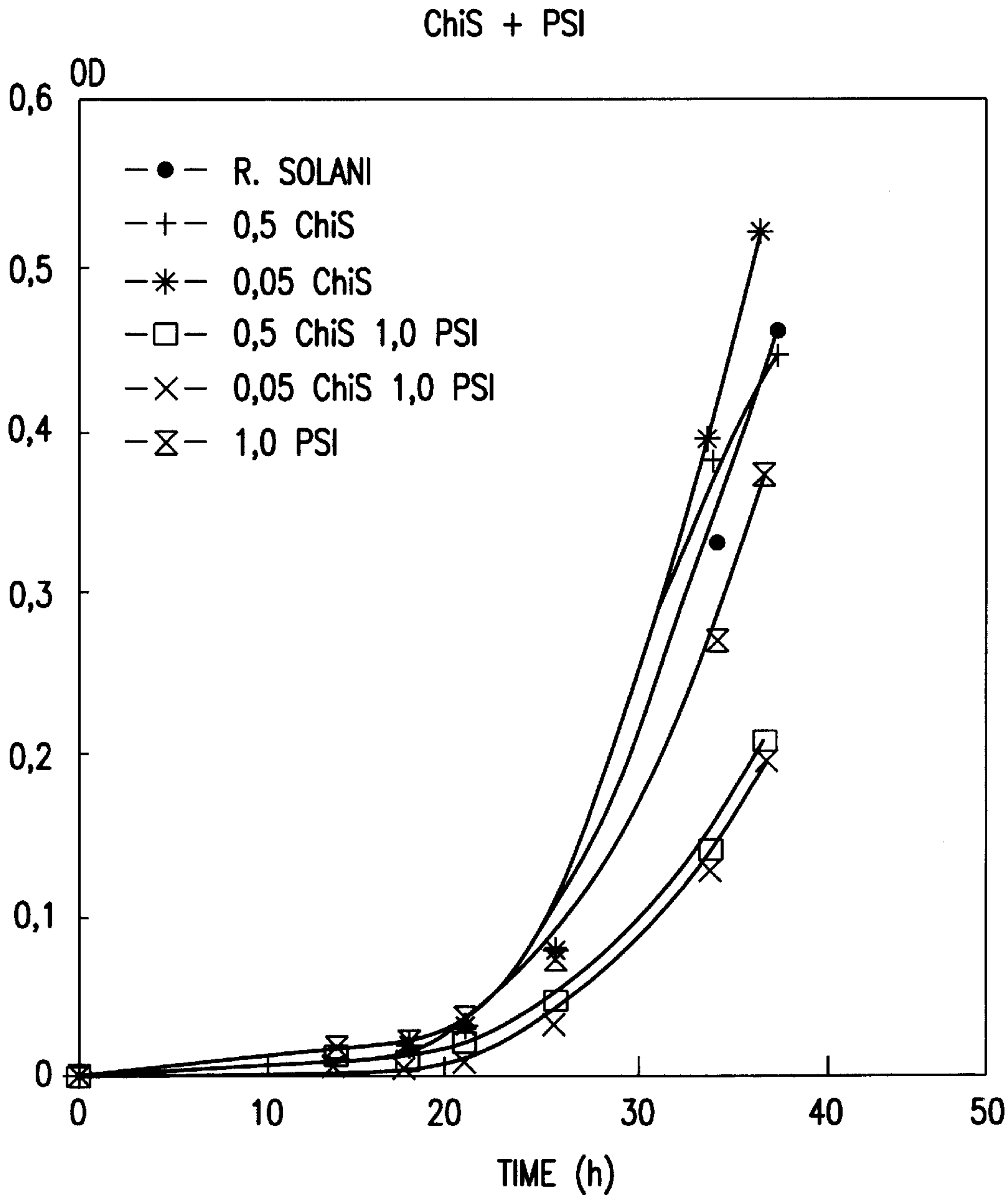
FIG. 2 shows the effects of ChiS and PSA on *Rhizoctonia solani.*

The AFP and PSI combination also according to this shows a synergistic inhibition of growth of the fungus R. Solani. FIG. 2 indicates the test results with various AFP concentrations (0.4 $\mu$g/ml and 0.04 $\mu$g/ml) combined with PSI protein (1.0 $\mu$g/ml).

EXAMPLE 2

Transgenic plants

In order to obtain the organisms according to the invention with DNA sequences which act together synergistically, initially transgenic plants which contained at least one of the genes which act together synergistically were generated.

ChiS in transgenic plants

Initially a ChiS gene was fused to plant regulatory sequences.

A ChiS gene 1.8 Kb in size was sequenced by using synthetic oligonucleotides in the dideoxy sequencing method of Sanger et al. in Proc. Natl. Acad. Sci. USA, 74 (1977), 5463–5467.

The 35S promoter originating from cauliflower mosaic virus (CamV) (400 bp (according to Töpfer et al. in Nucl. Acid. Res., 15 (1987), 5890)) underwent transcriptional fusion to the ChiS gene. The termination signal, which is 0.2 Kb in size, of the 35S gene of CamV, whose functionality in dicotyledonous plants is known, was used 3' from the ChiS gene. The chimeric gene 35S-ChiS was closed into the pLS034 vector by means of the Agrobacterium tumefaciens transformation system in tobacco and potato plants, and kanamycin-resistant plants were regenerated.

It was possible to detect both the ChiS gene and the corresponding mRNA as well as the gene product protein in the resulting plants.

PSI in transgenic plants

PolyA$^-$ RNA was initially isolated from ripe barley seeds (Hordeum vulgare L. cv. Piggy) and deposited in a cDNA gene bank in λ-gt-11-phages. The details of the process are to be found in R. Lea in Plant. Biol., 12 (1989), 673–682. Monospecific PSI antibodies were then used to identify cDNA clones.

Subsequently, the PSI-positive λ-gt-11-phages wee isolated, cloned further and sequenced by the dideoxy sequencing method of Sanger et al. indicated above. The DNA cloned into *E. coli* was then transferred in the manner described above by conjugation into Agrobacterium LBA4404.

Both the Transferred gene and mRNA and gene product were detectable in corresponding transgenic tobacco, potato, rape, strawberry and tomato plants.

AFP in transgenic plants

For the cloning in the vector, the cDNA sequence of the antifungal peptide is provided with ends which can be ligated into BamH1 and Sal1 restriction cleavage sites. The cloning vector used was pDH51 (Pietrzak et al. in Nucl. Acids Res. 14 (1986), 5857). The vector pDH51 was opened with the restriction enzymes BamH1 and Sal1 between promoter and terminator. The vector pDH51 is a pUC18 derivative which contains promoter and terminator sequences of the 35S transcript from cauliflower mosaic virus. These sequences are recognized by the plant's transcription apparatus and lead to strong constitutive expression of the gene associated with them in plants. The DNA of the antifungal peptide is then cloned via the BamH1 and Sal1 cleavage site into the vector. Finally, the transcription unit—promoter, gene and terminator—is cut out of the vector using the restriction enzyme EcoRI and cloned into a plant transformation vector. The following vectors and their derivatives can, for example, be used as plant transformation vector:

pOCA18 (Olszewski et al. in Nucl. Acids Res., 16 (1988), 10765) pPCV310 (Koncz and Shell in MGG 204 (1986), 383) and pBin19 (Bevan et al. Nucl. Acids. Res. 12 (1984), 8711).

After the transcription unit and the vector had been ligated via the EcoRI cleavage site, the construct was conjugated into the Agrobacterium strain MP90RK (Koncz and Shell (see above)) or IHA101 (Hood et al. in J. Bacteriol. 168 (1986), 1291).

Transgenic tobacco, potato, strawberry, rape and tomato plants were then transformed by the method described above. Transformed shoots are selected on the basis of the cotransferred resistance to the antibiotic kanamycin. Expression of the antifungal protein in the transformed crop plants was checked and confirmed by DNA analysis (Southern blotting), RNA analysis (Northern blotting) and protein analysis with specific antibodies (Western blotting).

ChiG and GluG in transgenic plants

ChiG- and GluG-transgenic plants which were both Southern-, Northern- and Western-positive were obtainable in analogy to the plants described above.

ChiS, PSI, AFP, ChiG, GluG in transgenic monocotyledonous plants

It was possible by means of direct gene transfer to integrate the abovementioned genes into the genome of monocotyledonous plants such as, for example, corn. This resulted in transgenic plants which were Southern- and Northern- and Western-positive.

Combination of various fungus-resistance genes in transgenic plants

The previously obtained tobacco, corn, rape, strawberry, potato and tomato plants were crossed together and selected for plants containing in each case the fungus-resistant genes of both parents. In addition, transgenic plants were obtained by transforming them initially with one and then with one or more other gene. Finally, plants were also transformed with vectors which contained various resistance genes. Fungus-resistance tests were done with this plant material. Surprisingly, in all cases synergistic effects, not just additive effects, in respect of fungus resistance are observed.

For example, a tobacco plant which expresses ChiS and PSI shows a considerably greater resistance to Rhizoctonia infestation than the plants which expressed only ChiS or PSI or which would result from the additive resistance.

A synergistic inhibitory effect on infestation with *Rhizoctonia solani* also results from combined expression of PSI- and AFP-transgenic tobacco. Combination of two or more different genes (ChiS, RIP, AFP, ChiG and GluG) in a wide variety of transgenic plants also led to synergistic inhibitory effects on various fungi.

Whereas wild-type plants have index values from 38 to 46 in tests on 20 seedlings, it emerges with transgenic tobacco according to the invention that the latter grows as well in the presence of the fungus *Rhizoctonia solani* as do control plants (index value 10–12) cultivated on Rhizoctonia-free soil.

What is claimed is:

1. A transgenic plant comprising:

(i) at least one DNA sequence, operably linked to a plant-functional promoter, said DNA sequence encoding a protein selected from the group consisting of:

a ChiG protein comprising the sequence as set forth in SEQUENCE ID No. 10, a GluG protein comprising the sequence as set forth in SEQUENCE ID NO; 12, a PSI protein comprising the sequence as set forth in SEQUENCE ID NO; 5 or 7, and an AFP protein comprising the sequence as set forth in SEQUENCE ID NO. 3, and (ii) a DNA sequence encoding a ChiS protein which is the gene product of the sequence as set forth in SEQUENCE ID NO. 8, operably linked to a plant-functional promoter, wherein the plant is resistant to fungal attack.

2. A transgenic plant comprising:

(i) at least one DNA sequence, operably linked to a plant-functional promoter, said DNA sequence encoding a protein selected from the group consisting of:

a ChiG protein comprising the sequence as set forth in SEQUENCE ID NO. 10, a GluG protein comprising the sequence as set forth in SEQUENCE ID NO. 12, a PSI protein comprising the sequence as set forth in SEQUENCE ID NO. 5 or 7, and a ChiS protein which is the gene product of the sequence as set forth in SEQUENCE ID NO. 8, and (ii) a DNA sequence encoding an AFP protein comprising the sequence as set forth in SEQUENCE ID NO. 3, operably linked to a plant-functional promoter, wherein the plant is resistant to fungal attack.

3. A transgenic fungus-resistant plant according to claim 1 or 2, wherein the plant is a tobacco, potato, strawberry, corn, rape or tomato plant.

4. A purified and isolated DNA molecule comprising:

(i) at least one DNA sequence, operably linked to a plant-functional promoter, said DNA sequence encoding a protein selected from the group consisting of:

a ChiG protein comprising the sequence as set forth in SEQUENCE ID NO. 10, a GluG protein comprising the sequence as set forth in SEQUENCE ID NO. 12, a PSI protein comprising the sequence as set forth in SEQUENCE ID NO. 5 or 7, and an AFP protein comprising the sequence as set forth in SEQUENCE ID NO. 3, and (ii) a DNA sequence encoding a ChiS protein which is the gene product of the sequence as set forth in SEQUENCE ID NO. 8.

5. A purified and isolated DNA molecule comprising (i) at least one DNA sequence, operably linked to a plant-functional promoter, said DNA sequence encoding a protein selected from the group consisting of:

a ChiG protein comprising the sequence as set forth in SEQUENCE ID NO. 10, a GluG protein comprising the sequence as set forth in SEQUENCE ID NO. 12, a PSI protein comprising the sequence as set forth in SEQUENCE ID NO. 5 or 7, and a ChiS protein which is the gene product of the sequence as set forth in SEQUENCE ID NO. 8, and (ii) a DNA sequence encoding an AFP protein comprising the sequence as set forth in SEQUENCE ID NO. 3.

6. The fungus-resistant plant of claim 1 or 2, which is obtained by a method selected from the group consisting of (i) crossing of two transgenic plants, each containing at least one of said DNA sequences of claim 1 or 2, and subsequently selecting the fungus-resistant plant, and (ii) transforming a plant with each of said DNA sequences of claim 1 or 2.

7. A process for the generation of a transgenic fungus-resistant plant, comprising transforming a plant with:

(i) at least one DNA sequence, operably linked to a plant-functional promoter, said DNA sequence encoding a protein selected from the group consisting of:

a ChiG protein comprising the sequence as set forth in SEQUENCE ID NO. 10, a GluG protein comprising the sequence as set forth in SEQUENCE ID NO. 12, a PSI protein comprising the sequence as set forth in SEQUENCE ID NO. 5 or 7, and an AFP protein comprising the sequence as set forth in SEQUENCE ID NO. 3, and (ii) a DNA sequence encoding a ChiS protein which is the gene product of the sequence as set forth in SEQUENCE ID NO. 8, operably linked to a plant-functional promoter.

8. A process for the generation of a transgenic fungus-resistant plant, comprising transforming a plant with:

(i) at least one DNA sequence, operably linked to a plant-functional promoter, said DNA sequence encoding a protein selected from the group consisting of:

a ChiG protein comprising the sequence as set forth in SEQUENCE ID NO. 10, a GluG protein comprising the sequence as set forth in SEQUENCE ID NO. 12, a PSI protein comprising the sequence as set forth in SEQUENCE ID NO. 5 or 7, and a ChiS protein which is the gene product of the sequence as set forth in SEQUENCE ID NO. 8, and (ii) a DNA sequence encoding an AFP protein comprising the sequence as set forth in SEQUENCE ID NO. 3, operably linked to a plant-functional promoter.

9. A process for the generation of a fungus-resistant plant, said method selected from the group consisting of:

(i) crossing of two transgenic plants, each containing at least one of said DNA sequences of claim 7 or 8, and subsequently selecting the fungus-resistant plant, and (ii) transforming a plant with each of said DNA sequences of claim 7 in 8.

10. A transgenic plant, comprising 2 transgenes, each operably linked to a plant-functional promoter, said transgenes encoding a protein selected from the group consisting of:

(i) a PSI protein comprising the sequence of set forth in SEQUENCE ID NO. 5 to 7, and (ii) an AFP protein comprising the sequence as set forth in SEQUENCE ID NO. 3.

11. The plant of claim 10 whose resistance to fungal pathogens is increased overall by comparison with the known nontransgenic plant.

12. The plant of claim 10 or 11 which is corn.

13. The plant of claim 1 or 2 wherein said DNA sequence is of natural, synthetic or semisynthetic origin.

* * * * *

UNITED STATES PATENT AND TRADEMARK OFFICE

CERTIFICATE OF CORRECTION

PATENT NO. : 6,271,438 B1
DATED : August 7, 2001
INVENTOR(S) : Logemann et al.

It is certified that error appears in the above-identified patent and that said Letters Patent is hereby corrected as shown below:

Title page,
Item [57], ABSTRACT, line 6, "chitinese" should read -- chitinase --
Line 8, "(AFR)." should read -- (AFP). --

Column 2,
Line 37, "ChiS" should read -- ¶ChiS --
Line 39, "(EQ ID NO:8)" should read -- (SEQ ID NO:8) --
Line 41, "sowed" should read -- showed --
Line 46, "PSI" should read -- ¶PSI --

Column 3,
Line 1, "virto" should read -- vitro --
Line 6, "completely," should read -- completely --
Line 18, "luG." should read -- GluG. --
Line 37, "abovemented" should read -- abovementioned --
Line 58, "were" should read -- also --

Column 4,
Line 4, "is each," should read -- in each --
Line 42, "bacteria" should read -- bacteria, --
Line 44, "trangenic" should read -- transgenic --
Line 52, "however." should read -- however, --
Line 53, "Also" should read -- also --

Column 5,
Line 1, "NO;6;" should read -- NO:6; --
Line 22, "certification" should read -- centrifugation --
Line 37, "HAP=0.1" should read -- BAP + 0.1 --
Line 47, "(Example)" should read -- (Example: --

Column 7,
Line 48, "R. Lea" should read -- R. Leah --
Line 57, "Transferred" should read -- transferred --

UNITED STATES PATENT AND TRADEMARK OFFICE

CERTIFICATE OF CORRECTION

PATENT NO. : 6,271,438 B1
DATED : August 7, 2001
INVENTOR(S) : Logemann et al.

It is certified that error appears in the above-identified patent and that said Letters Patent is hereby corrected as shown below:

Column 33,
Line 47, "No." should read -- NO. --
Line 48, "No." should read -- NO. --
Line 50, "No." should read -- NO. --

Signed and Sealed this

Seventh Day of May, 2002

*Attest:*

JAMES E. ROGAN
*Director of the United States Patent and Trademark Office*

*Attesting Officer*

SEQUENCE LISTING

```
(1) GENERAL INFORMATION:

   (iii) NUMBER OF SEQUENCES: 12


(2) INFORMATION FOR SEQ ID NO: 1:

     (i) SEQUENCE CHARACTERISTICS:
          (A) LENGTH: 275 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Aspergillus giganteus

    (ix) FEATURE:
          (A) NAME/KEY: 5'UTR
          (B) LOCATION: 1..45

    (ix) FEATURE:
          (A) NAME/KEY: CDS
          (B) LOCATION: 46..225
          (C) IDENTIFICATION METHOD: experimental
          (D) OTHER INFORMATION: /codon_start= 46 /function= "antifungal
              agent" /product= "antifungal peptide)" /evidence=
              EXPERIMENTAL /note= "antifungal agent, especially on
              Rhizoctonia solani, various Aspergillus, Fusaria and
              Trichophyton species"

    (xi) SEQUENCE DESCRIPTION: SEQ ID NO: 1:

TTGCCACCCC CGTTGAAGCC GATTCTCTCA CCGCTGGTGG TCTGG ATG CAA GAG         54
                                                  Met Gln Glu
                                                    1

ATG AGA GCG CGG GTT TTG GCC ACA TAC AAT GGC AAA TGC TAC AAG AAG      102
Met Arg Ala Arg Val Leu Ala Thr Tyr Asn Gly Lys Cys Tyr Lys Lys
      5                  10                  15

GAT AAT ATC TGC AAG TAC AAG GCA CAG AGC GGC AAG ACT GCC ATT TGC      150
Asp Asn Ile Cys Lys Tyr Lys Ala Gln Ser Gly Lys Thr Ala Ile Cys
 20                  25                  30                  35

AAG TGC TAT GTC AAA AAG TGC CCC CGC GAC GGC GCG AAA TGC GAG TTT      198
Lys Cys Tyr Val Lys Lys Cys Pro Arg Asp Gly Ala Lys Cys Glu Phe
                 40                  45                  50

GAC AGC TAC AAG GGG AAG TGC TAC TGC TAGACGGTGA GCGAAGGGAC            245
Asp Ser Tyr Lys Gly Lys Cys Tyr Cys
             55                  60

GAAGTAGGCT GGGGGTTATT TTACTCTGCT                                     275


(2) INFORMATION FOR SEQ ID NO: 2:

     (i) SEQUENCE CHARACTERISTICS:
          (A) LENGTH: 60 amino acids
          (B) TYPE: amino acid
          (D) TOPOLOGY: linear

    (ii) MOLECULE TYPE: protein

    (xi) SEQUENCE DESCRIPTION: SEQ ID NO: 2:

Met Gln Glu Met Arg Ala Arg Val Leu Ala Thr Tyr Asn Gly Lys Cys
  1               5                  10                  15

Tyr Lys Lys Asp Asn Ile Cys Lys Tyr Lys Ala Gln Ser Gly Lys Thr
             20                  25                  30

Ala Ile Cys Lys Cys Tyr Val Lys Lys Cys Pro Arg Asp Gly Ala Lys
         35                  40                  45
```

-continued

```
Cys Glu Phe Asp Ser Tyr Lys Gly Lys Cys Tyr Cys
     50                  55                  60
```

(2) INFORMATION FOR SEQ ID NO: 3:

(i) SEQUENCE CHARACTERISTICS:
(A) LENGTH: 51 amino acids
(B) TYPE: amino acid
(D) TOPOLOGY: linear (ii) MOLECULE TYPE: protein (v) FRAGMENT TYPE: C-terminal (vi) ORIGINAL SOURCE:
(A) ORGANISM: Aspergillus giganteus (ix) FEATURE:
(A) NAME/KEY: Protein
(B) LOCATION: 1..51
(D) OTHER INFORMATION: /note= “active protein fragment of AFP”

(xi) SEQUENCE DESCRIPTION: SEQ ID NO: 3:

```
Ala Thr Tyr Asn Gly Lys Cys Tyr Lys Lys Asp Asn Ile Cys Lys Tyr
1               5                   10                  15

Lys Ala Gln Ser Gly Lys Thr Ala Ile Cys Lys Cys Tyr Val Lys Lys
            20                  25                  30

Cys Pro Arg Asp Gly Ala Lys Cys Glu Phe Asp Ser Tyr Lys Gly Lys
        35                  40                  45

Cys Tyr Cys
    50
```

(2) INFORMATION FOR SEQ ID NO: 4:

(i) SEQUENCE CHARACTERISTICS:
(A) LENGTH: 1032 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Hordeum vulgare
(B) STRAIN: L.cv. Piggy (vii) IMMEDIATE SOURCE:
(A) LIBRARY: cDNA gene bank in lambda-gt-11-phages (ix) FEATURE:
(A) NAME/KEY: 5'UTR
(B) LOCATION: 1..42

(ix) FEATURE:
(A) NAME/KEY: CDS
(B) LOCATION: 43..885
(D) OTHER INFORMATION: /codon_start= 43 /function= “antifungal activity” /product= “protein synthesis inhibitor (PSI)” /note= “antifungal activity, especially on spores of Trichoderma reesii and Fusarium sporotrichoides and on Rhizoctonia solani.”

(ix) FEATURE:
(A) NAME/KEY: 3'UTR
(B) LOCATION: 886..1032
(D) OTHER INFORMATION: /partial /note= “46 nucleotides at the 3'-end not shown.”

(ix) FEATURE:
(A) NAME/KEY: polyA_signal
(B) LOCATION: 930..935
(D) OTHER INFORMATION: /note= “potential polyadenylation signal”

-continued

```
    (ix) FEATURE:
          (A) NAME/KEY: polyA_signal
          (B) LOCATION: 963..976
          (D) OTHER INFORMATION: /note= "potential polyadenylation
              signal"

    (ix) FEATURE:
          (A) NAME/KEY: polyA_signal
          (B) LOCATION: 1002..1011
          (D) OTHER INFORMATION: /note= "potential polyadenylation
              signal"

    (ix) FEATURE:
          (A) NAME/KEY: mat_peptide
          (B) LOCATION: 46..886

    (xi) SEQUENCE DESCRIPTION: SEQ ID NO: 4:

CTTAATAGCA CATCTTGTCC GTCTTAGCTT TGCATTACAT CC ATG GCG GCA AAG         54
                                               Met Ala Ala Lys
                                                 1

ATG GCG AAG AAC GTG GAC AAG CCG CTC TTC ACC GCG ACG TTC AAC GTC       102
Met Ala Lys Asn Val Asp Lys Pro Leu Phe Thr Ala Thr Phe Asn Val
  5                  10                  15                  20

CAG GCC AGC TCC GCC GAC TAC GCC ACC TTC ATC GCC GGC ATC CGC AAC       150
Gln Ala Ser Ser Ala Asp Tyr Ala Thr Phe Ile Ala Gly Ile Arg Asn
                 25                  30                  35

AAG CTC CGC AAC CCG GCG CAC TTC TCC CAC AAC CGC CCC GTG CTG CCG       198
Lys Leu Arg Asn Pro Ala His Phe Ser His Asn Arg Pro Val Leu Pro
             40                  45                  50

CCG GTC GAG CCC AAC GTC CCG CCG AGC AGG TGG TTC CAC GTC GTG CTC       246
Pro Val Glu Pro Asn Val Pro Pro Ser Arg Trp Phe His Val Val Leu
         55                  60                  65

AAG GCC TCG CCG ACC AGC GCC GGG CTC ACG CTG GCC ATT CGG GCG GAC       294
Lys Ala Ser Pro Thr Ser Ala Gly Leu Thr Leu Ala Ile Arg Ala Asp
     70                  75                  80

AAC ATC TAC CTG GAG GGC TTC AAG AGC AGC GAC GGC ACC TGG TGG GAG       342
Asn Ile Tyr Leu Glu Gly Phe Lys Ser Ser Asp Gly Thr Trp Trp Glu
 85                  90                  95                 100

CTC ACC CCG GGC CTC ATC CCC GGC GCC ACC TAC GTC GGG TTC GGC GGC       390
Leu Thr Pro Gly Leu Ile Pro Gly Ala Thr Tyr Val Gly Phe Gly Gly
                105                 110                 115

ACC TAC CGC GAC CTC CTC GGC GAC ACC GAC AAG CTG ACC AAC GTC GCT       438
Thr Tyr Arg Asp Leu Leu Gly Asp Thr Asp Lys Leu Thr Asn Val Ala
            120                 125                 130

CTC GGC CGG CAG CAG CTG GCG GAC GCG GTG ACC GCC CTC CAC GGG CGC       486
Leu Gly Arg Gln Gln Leu Ala Asp Ala Val Thr Ala Leu His Gly Arg
        135                 140                 145

ACC AAG GCC GAC AAG CCG TCC GGC CCG AAG CAG CAG CAG GCG AGG GAG       534
Thr Lys Ala Asp Lys Pro Ser Gly Pro Lys Gln Gln Gln Ala Arg Glu
    150                 155                 160

GCG GTG ACG ACG CTG CTC CTC ATG GTG AAC GAG GCC ACG CGG TTC CAG       582
Ala Val Thr Thr Leu Leu Leu Met Val Asn Glu Ala Thr Arg Phe Gln
165                 170                 175                 180

ACG GTG TCT GGG TTC GTG GCC GGG TTG CTG CAC CCC AAG GCG GTG GAG       630
Thr Val Ser Gly Phe Val Ala Gly Leu Leu His Pro Lys Ala Val Glu
                185                 190                 195

AAG AAG AGC GGG AAG ATC GGC AAT GAG ATG AAG GCC CAG GTG AAC GGG       678
Lys Lys Ser Gly Lys Ile Gly Asn Glu Met Lys Ala Gln Val Asn Gly
            200                 205                 210

TGG CAG GAC CTG TCC GCG GCG CTG CTG AAG ACG GAC GTG AAG CCT CCG       726
Trp Gln Asp Leu Ser Ala Ala Leu Leu Lys Thr Asp Val Lys Pro Pro
        215                 220                 225
```

-continued

```
CCG GGA AAG TCG CCA GCG AAG TTC GCG CCG ATC GAG AAG ATG GGC GTG       774
Pro Gly Lys Ser Pro Ala Lys Phe Ala Pro Ile Glu Lys Met Gly Val
    230                 235                 240

AGG ACG GCT GTA CAG GCC GCC AAC ACG CTG GGG ATC CTG CTG TTC GTG       822
Arg Thr Ala Val Gln Ala Ala Asn Thr Leu Gly Ile Leu Leu Phe Val
245                 250                 255                 260

GAG GTG CCG GGT GGG TTG ACG GTG GCC AAG GCG CTG GAG CTG TTC CAT       870
Glu Val Pro Gly Gly Leu Thr Val Ala Lys Ala Leu Glu Leu Phe His
                265                 270                 275

GCG AGT GGT GGG AAA TAGGTAGTTT TCCAGGTATA CCTGCATGGG TAGTGTAAAA       925
Ala Ser Gly Gly Lys
            280

GTCGAATAAA CATGTCACAG AGTGACGGAC TGATATAAAT AAATAAATAA ACGTGTCACA    985

GAGTTACATA TAAACAAATA AATAAATAAT TAAAAATGTC CAGTTTA                 1032
```

(2) INFORMATION FOR SEQ ID NO: 5:

(i) SEQUENCE CHARACTERISTICS:
(A) LENGTH: 281 amino acids
(B) TYPE: amino acid
(D) TOPOLOGY: linear (ii) MOLECULE TYPE: protein (xi) SEQUENCE DESCRIPTION: SEQ ID NO: 5:

```
Met Ala Ala Lys Met Ala Lys Asn Val Asp Lys Pro Leu Phe Thr Ala
  1               5                  10                  15

Thr Phe Asn Val Gln Ala Ser Ser Ala Asp Tyr Ala Thr Phe Ile Ala
             20                  25                  30

Gly Ile Arg Asn Lys Leu Arg Asn Pro Ala His Phe Ser His Asn Arg
         35                  40                  45

Pro Val Leu Pro Pro Val Glu Pro Asn Val Pro Pro Ser Arg Trp Phe
     50                  55                  60

His Val Val Leu Lys Ala Ser Pro Thr Ser Ala Gly Leu Thr Leu Ala
 65                  70                  75                  80

Ile Arg Ala Asp Asn Ile Tyr Leu Glu Gly Phe Lys Ser Ser Asp Gly
                 85                  90                  95

Thr Trp Trp Glu Leu Thr Pro Gly Leu Ile Pro Gly Ala Thr Tyr Val
            100                 105                 110

Gly Phe Gly Gly Thr Tyr Arg Asp Leu Leu Gly Asp Thr Asp Lys Leu
        115                 120                 125

Thr Asn Val Ala Leu Gly Arg Gln Gln Leu Ala Asp Ala Val Thr Ala
    130                 135                 140

Leu His Gly Arg Thr Lys Ala Asp Lys Pro Ser Gly Pro Lys Gln Gln
145                 150                 155                 160

Gln Ala Arg Glu Ala Val Thr Thr Leu Leu Leu Met Val Asn Glu Ala
                165                 170                 175

Thr Arg Phe Gln Thr Val Ser Gly Phe Val Ala Gly Leu Leu His Pro
            180                 185                 190

Lys Ala Val Glu Lys Lys Ser Gly Lys Ile Gly Asn Glu Met Lys Ala
        195                 200                 205

Gln Val Asn Gly Trp Gln Asp Leu Ser Ala Ala Leu Leu Lys Thr Asp
    210                 215                 220

Val Lys Pro Pro Pro Gly Lys Ser Pro Ala Lys Phe Ala Pro Ile Glu
225                 230                 235                 240

Lys Met Gly Val Arg Thr Ala Val Gln Ala Ala Asn Thr Leu Gly Ile
                245                 250                 255
```

-continued

```
Leu Leu Phe Val Glu Val Pro Gly Gly Leu Thr Val Ala Lys Ala Leu
            260                 265                 270

Glu Leu Phe His Ala Ser Gly Gly Lys


(2) INFORMATION FOR SEQ ID NO: 6:

     (i) SEQUENCE CHARACTERISTICS:
          (A) LENGTH: 480 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Hordeum vulgare
          (B) STRAIN: L.cv. Piggy

   (vii) IMMEDIATE SOURCE:
          (A) LIBRARY: cDNA gene bank in lambda-gt-11-phages
          (B) CLONE: incomplete psi cDNA clone

    (ix) FEATURE:
          (A) NAME/KEY: CDS
          (B) LOCATION: 1..351
          (D) OTHER INFORMATION: /partial /codon_start= 1 /function=
              "protein synthesis inhibitor" /product= "protein synthesis
              inhibitor" /standard_name= "PSI" /note= "aminoterminally
              incomplete protein from an incomplete PSI cDNA clone"

    (ix) FEATURE:
          (A) NAME/KEY: 3'UTR
          (B) LOCATION: 352..487

    (ix) FEATURE:
          (A) NAME/KEY: polyA_signal
          (B) LOCATION: 404..409
          (D) OTHER INFORMATION: /note= "potential polyadenylation
              signal"

    (ix) FEATURE:
          (A) NAME/KEY: polyA_signal
          (B) LOCATION: 437..442
          (D) OTHER INFORMATION: /note= "potential polyadenylation
              signal"

    (ix) FEATURE:
          (A) NAME/KEY: polyA_signal
          (B) LOCATION: 445..450
          (D) OTHER INFORMATION: /note= "potential polyadenylation
              signal"

    (xi) SEQUENCE DESCRIPTION: SEQ ID NO: 6:

GCG GTG ACG ACG CTG CTC CTC ATG GTG AAC GAG GCC ACG CGG TTC CAG       48
Ala Val Thr Thr Leu Leu Leu Met Val Asn Glu Ala Thr Arg Phe Gln
  1               5                  10                  15

ACG GTG TCG GGG TTC GTG GCC GGG CTG CTG CAC CCC AAG GCG GTG GAG       96
Thr Val Ser Gly Phe Val Ala Gly Leu Leu His Pro Lys Ala Val Glu
            20                  25                  30

AAG AAG AGC GGG AAG ATC GGC AAT GAG ATG AAG GCC CAG GTG AAC GGG      144
Lys Lys Ser Gly Lys Ile Gly Asn Glu Met Lys Ala Gln Val Asn Gly
        35                  40                  45

TGG CAG GAC CTG TCC GCG GCG CTG CTG AAG ACG GAC GTG AAG CCC CCG      192
Trp Gln Asp Leu Ser Ala Ala Leu Leu Lys Thr Asp Val Lys Pro Pro
     50                  55                  60

CCG GGA AAG TCG CCA GCG AAG TTC ACG CCG ATC GAG AAG ATG GGC GTG      240
Pro Gly Lys Ser Pro Ala Lys Phe Thr Pro Ile Glu Lys Met Gly Val
 65                  70                  75                  80

AGG ACT GCT GAG CAG GCT GCG GCT ACT TTG GGG ATC CTG CTG TTC GTT      288
Arg Thr Ala Glu Gln Ala Ala Ala Thr Leu Gly Ile Leu Leu Phe Val
                 85                  90                  95
```

-continued

```
GAG GTG CCG GGT GGG TTG ACG GTG GCC AAG GCG CTG GAG CTG TTT CAT      336
Glu Val Pro Gly Gly Leu Thr Val Ala Lys Ala Leu Glu Leu Phe His
            100                 105                 110

GCG AGT GGT GGG AAA TAGGTAGTTT TGCAGGTATA CCTGCATGGG TAAATGTAAA      391
Ala Ser Gly Gly Lys
        115

AGTCGAATAA AAATGTCACA GAGTGACGGA CTGATATAAA TAAATTAATA AACATGTCAT    451

CATGAGTGAC AGACTGATAT AAATAAATA                                      480
```

(2) INFORMATION FOR SEQ ID NO: 7:

(i) SEQUENCE CHARACTERISTICS:
(A) LENGTH: 117 amino acids
(B) TYPE: amino acid
(D) TOPOLOGY: linear (ii) MOLECULE TYPE: protein (xi) SEQUENCE DESCRIPTION: SEQ ID NO: 7:

```
Ala Val Thr Thr Leu Leu Leu Met Val Asn Glu Ala Thr Arg Phe Gln
  1               5                  10                  15

Thr Val Ser Gly Phe Val Ala Gly Leu Leu His Pro Lys Ala Val Glu
             20                  25                  30

Lys Lys Ser Gly Lys Ile Gly Asn Glu Met Lys Ala Gln Val Asn Gly
         35                  40                  45

Trp Gln Asp Leu Ser Ala Ala Leu Leu Lys Thr Asp Val Lys Pro Pro
     50                  55                  60

Pro Gly Lys Ser Pro Ala Lys Phe Thr Pro Ile Glu Lys Met Gly Val
 65                  70                  75                  80

Arg Thr Ala Glu Gln Ala Ala Ala Thr Leu Gly Ile Leu Leu Phe Val
                 85                  90                  95

Glu Val Pro Gly Gly Leu Thr Val Ala Lys Ala Leu Glu Leu Phe His
            100                 105                 110

Ala Ser Gly Gly Lys
        115
```

(2) INFORMATION FOR SEQ ID NO: 8:

(i) SEQUENCE CHARACTERISTICS:
(A) LENGTH: 2329 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Serratia marcescens (vii) IMMEDIATE SOURCE:
(A) LIBRARY: Cosmid bank from Serratia marcescens (ix) FEATURE:
(A) NAME/KEY: misc_feature
(B) LOCATION: 1..2329
(C) IDENTIFICATION METHOD: experimental
(D) OTHER INFORMATION: /function= "exo-chitinase" /product= "ChiS protein" /evidence= EXPERIMENTAL /note= "sequence listing of the ChiS gene from a plasmid pLChiS from E.coli A 5187"

(xi) SEQUENCE DESCRIPTION: SEQ ID NO: 8:

```
CAGGGCGTTG TCAATAATGA CAACACCCTG GCTGAAGAGT GTGGTGCAAT ACTGATAAAT     60

ATTTATCTTT CCTTAATAGA AAATTCACTA TCCTTATTTG TCATGTTTTC TTTTATTTAT    120
```

-continued

```
ATGAAAATAA ATTCACGCTT GCTGAATAAA ACCCAGTTGA TAGCGCTCTT GTTTTTGCGC    180
CTTTTTTATT TATAGTACTG AATGTACGCG GTGGGAATGA TTATTTCGCC ACGTGGAAAG    240
ACGCTGTTGT TATTTATTGA TTTTAACCTT CGCGGATTAT TGCGGAATTT TTTCGCTTCG    300
GCAATGCATC GCGACGATTA ACTCTTTTAT GTTTATCCTC TCGGAATAAA GGAATCAGTT    360
ATGCGCAAAT TTAATAAACC GCTGTTGGCG CTGTTGATCG GCAGCACGCT GTGTTCCGCG    420
GCGCAGGCCG CCGCGCCGGG CAAGCCGACC ATCGCCTGGG GCAACACCAA GTTCGCCATC    480
GTTGAAGTTG ACCAGGCGGC TACCGCTTAT AATAATTTGG TGAAGGTAAA AAATGCCGCC    540
GATGTTTCCG TCTCCTGGAA TTTATGGAAT GGCGACACCG GCACGACGGC AAAAGTTTTA    600
TTAAATGGCA AAGAGGCGTG GAGTGGTCCT TCAACCGGAT CTTCCGGTAC GGCGAATTTT    660
AAAGTGAATA AAGGCGGCCG TTATCAAATG CAGGTGGCAC TGTGCAATGC CGACGGCTGC    720
ACCGCCAGTG ACGCCACCGA AATTGTGGTA GCCGACACCG ACGGCAGCCA TTTGGCGCCG    780
TTGAAAGAGC CGCTGCTGGA AAAGAATAAA CCGTATAAAC AGAACTCCGG CAAAGTGGTC    840
GGTTCTTATT TCGTCGAGTG GGGCGTTTAC GGGCGCAATT TCACCGTCGA CAAGATCCCG    900
GCGCAAAACC TGACCCACCT GCTGTACGGC TTTATCCCGA TCTGCGGCGG CAATGGCATC    960
AACGACAGCC TGAAAGAGAT TGAAGGCAGC TTCCAGGCGT TGCAGCGCTC CTGCCAGGGC   1020
CGCGAGGACT TCAAAGTCTC GATCCACGAT CCGTTCGCCC CGCTGCAAAA AGCGCAGAAG   1080
GGCGTGACCG CCTGGGATGA CCCCTACAAG GGCAACTTCG GCCAGCTGAT GGCGCTGAAG   1140
CAGGCGCATC CTGACCTGAA AATCCTGCCG TCGATCGGCG GCTGGACGCT GTCCGACCCG   1200
TTCTTCTTCA TGGGCGACAA GGTGAAGCGC GATCGCTTCG TCGGTTCGGT GAAAGAGTTC   1260
CTGCAGACCT GGAAGTTCTT CGACGGCGTG GATATCGACT GGGAGTTCCC GGGCGGCAAA   1320
GGCGCCAACC CTAACCTGGG CAGCCCGCAA GACGGGGAAA CCTATGTGCT GCTGATGAAG   1380
GAGCTGCGGG CGATGCTGGA TCAGCTGTCG GTGGAAACCG GCCGCAAGTA TGAGCTGACC   1440
TCCGCCATCA GCGCCGGTAA GGACAAGATC GACAAGGTGG CTTACAACGT TGCGCAGAAC   1500
TCGATGGATC ACATCTTCCT GATGAGCTAC GACTTCTATG GCGCCTTCGA TCTGAAGAAC   1560
CTGGGGCATC AGACCGCGCT GAATGCGCCG GCCTGGAAAC CGGACACCGC CTACACCACG   1620
GTGAACGGCG TCAATGCGCT GCTGGCGCAG GGCGTCAAGC CGGGCAAAAT CGTCGTCGGC   1680
ACCGCCATGT ATGGCCGCGG CTGGACCGGG GTGAACGGCT ACCAGAACAA TATTCCGTTC   1740
ACCGGCACCG CCACCGGGCC GGTTAAAGGC ACCTGGGAGA ACGGTATCGT GGACTACCGC   1800
CAAATCGCCG GCCAGTTCAT GAGCGGCGAG TGGCAGTATA CCTACGACGC CACGGCGGAA   1860
GCGCCTTACG TGTTCAAACC TTCCACCGGC GATCTGATCA CCTTCGACGA TGCCCGCTCG   1920
GTGCAGGCTA AAGGCAAGTA CGTGTTGGAT AAGCAGCTGG GCGGCCTGTT CTCCTGGGAG   1980
ATCGACGCGG ATAACGGCGA TATTCTCAAC AGCATGAACG CCAGCCTGGG CAACAGCGCC   2040
GGCGTTCAAT AATCGGTTGC AGTGGTTGCC GGGGGATATC CTTTCGCCCC CGGCTTTTTC   2100
GCCGACGAAA GTTTTTTTAC GCCGCACAGA TTGTGGCTCT GCCCCGAGCA AAACGCGCTC   2160
ATCGGACTCA CCCTTTTGGG TAATCCTTCA GCATTTCCTC CTGTCTTTAA CGGCGATCAC   2220
AAAAATAACC GTTCAGATAT TCATCATTCA GCAACAAAGT TTTGGCGTTT TTTAACGGAG   2280
TTAAAAACCA GTAAGTTTGT GAGGGTCAGA CCAATGCGCT AAAAATGGG               2329
```

-continued (2) INFORMATION FOR SEQ ID NO: 9:

(i) SEQUENCE CHARACTERISTICS:
(A) LENGTH: 1002 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Hordeum vulgare
(B) STRAIN: L.

(ix) FEATURE:
(A) NAME/KEY: 5'UTR
(B) LOCATION: 1..63

(ix) FEATURE:
(A) NAME/KEY: CDS
(B) LOCATION: 64..861
(D) OTHER INFORMATION: /codon_start= 64 /function= "chitinase" /product= "26 kD preprotein of chitinase G (ChiG)" /note= "antifungal activity, especially on Trichoderma reesii and Fusarium sporotrichoides as well as Rhizoctonia solani and Botrytis cinerea."

(ix) FEATURE:
(A) NAME/KEY: 3'UTR
(B) LOCATION: 862..1002
(D) OTHER INFORMATION: /partial /note= "11 nucleotides at 3' end not shown"

(ix) FEATURE:
(A) NAME/KEY: polyA_signal
(B) LOCATION: 905..910
(D) OTHER INFORMATION: /note= "potential polyadenylation signal"

(ix) FEATURE:
(A) NAME/KEY: sig_peptide
(B) LOCATION: 64..294
(D) OTHER INFORMATION: /note= "probable signal peptide sequence"

(ix) FEATURE:
(A) NAME/KEY: sig_peptide
(B) LOCATION: 298..312
(D) OTHER INFORMATION: /note= "probable signal peptide sequence"

(ix) FEATURE:
(A) NAME/KEY: sig_peptide
(B) LOCATION: 349..378
(D) OTHER INFORMATION: /note= "probable signal peptide sequence"

(ix) FEATURE:
(A) NAME/KEY: sig_peptide
(B) LOCATION: 466..588
(D) OTHER INFORMATION: /note= "probable signal peptide sequence"

(ix) FEATURE:
(A) NAME/KEY: sig_peptide
(B) LOCATION: 607..861
(D) OTHER INFORMATION: /note= "probable signal peptide sequence"

(ix) FEATURE:
(A) NAME/KEY: mat_peptide
(B) LOCATION: 133..861

-continued

```
    (xi) SEQUENCE DESCRIPTION: SEQ ID NO: 9:

CCTACGACAG TAGCGTAACG GTAAACACCG AGTACGGTAC TCTGTGCTTT GTTGGCTCGC     60

ACA ATG AGA TCG CTC GCG GTG GTG GTG GCC GTG GTA GCC ACG GTG GCC      108
    Met Arg Ser Leu Ala Val Val Val Ala Val Val Ala Thr Val Ala
    -23         -20                 -15                 -10

ATG GCC ATC GGC ACG GCG CGC GGC AGC GTG TCC TCC ATC GTC TCG CGC      156
Met Ala Ile Gly Thr Ala Arg Gly Ser Val Ser Ser Ile Val Ser Arg
             -5                   1               5

GCA CAG TTT GAC CGC ATG CTT CTC CAC CGC AAC GAC GGC GCC TGC CAG      204
Ala Gln Phe Asp Arg Met Leu Leu His Arg Asn Asp Gly Ala Cys Gln
     10                  15                  20

GCC AAG GGC TTC TAC ACC TAC GAC GCC TTC GTC GCC GCC GCA GCC GCC      252
Ala Lys Gly Phe Tyr Thr Tyr Asp Ala Phe Val Ala Ala Ala Ala Ala
 25                  30                  35                  40

TTC CCG GGC TTC GGC ACC ACC GGC AGC GCC GAC GCC CAG AAG CGC GAG      300
Phe Pro Gly Phe Gly Thr Thr Gly Ser Ala Asp Ala Gln Lys Arg Glu
                 45                  50                  55

GTG GCC GCC TTC CTA GCA CAG ACC TCC CAC GAG ACC ACC GGC GGG TGG      348
Val Ala Ala Phe Leu Ala Gln Thr Ser His Glu Thr Thr Gly Gly Trp
             60                  65                  70

GCG ACT GCA CCG GAC GGG GCC TTC GCC TGG GGC TAC TGC TTC AAG CAG      396
Ala Thr Ala Pro Asp Gly Ala Phe Ala Trp Gly Tyr Cys Phe Lys Gln
         75                  80                  85

GAA CGT GGC GCC TCC TCC GAC TAC TGC ACC CCG AGC GCA CAA TGG CCG      444
Glu Arg Gly Ala Ser Ser Asp Tyr Cys Thr Pro Ser Ala Gln Trp Pro
     90                  95                 100

TGC GCC CCC GGG AAG CGC TAC TAC GGC CGC GGG CCA ATC CAG CTC TCC      492
Cys Ala Pro Gly Lys Arg Tyr Tyr Gly Arg Gly Pro Ile Gln Leu Ser
105                 110                 115                 120

CAC AAC TAC AAC TAT GGA CCT GCC GGC CGG GCC ATC GGG GTC GAT CTG      540
His Asn Tyr Asn Tyr Gly Pro Ala Gly Arg Ala Ile Gly Val Asp Leu
                125                 130                 135

CTG GCC AAC CCG GAC CTG GTG GCC ACG GAC GCC ACT GTG GGC TTT AAG      588
Leu Ala Asn Pro Asp Leu Val Ala Thr Asp Ala Thr Val Gly Phe Lys
            140                 145                 150

ACG GCC ATC TGG TTC TGG ATG ACG GCG CAG CCG CCC AAG CCA TCG AGC      636
Thr Ala Ile Trp Phe Trp Met Thr Ala Gln Pro Pro Lys Pro Ser Ser
        155                 160                 165

CAT GCT GTG ATC GCC GGC CAG TGG AGC CCG TCA GGG GCT GAC CGG GCC      684
His Ala Val Ile Ala Gly Gln Trp Ser Pro Ser Gly Ala Asp Arg Ala
    170                 175                 180

GCA GGC CGG GTG CCC GGG TTT GGT GTG ATC ACC AAC ATC ATC AAC GGC      732
Ala Gly Arg Val Pro Gly Phe Gly Val Ile Thr Asn Ile Ile Asn Gly
185                 190                 195                 200

GGG ATC GAG TGC GGT CAC GGG CAG GAC AGC CGC GTC GCC GAT CGA ATC      780
Gly Ile Glu Cys Gly His Gly Gln Asp Ser Arg Val Ala Asp Arg Ile
                205                 210                 215

GGG TTT TAC AAG CGC TAC TGT GAC ATC CTC GGC GTT GGC TAC GGC AAC      828
Gly Phe Tyr Lys Arg Tyr Cys Asp Ile Leu Gly Val Gly Tyr Gly Asn
            220                 225                 230

AAC CTC GAT TGC TAC AGC CAG AGA CCC TTC GCC TAATTAATTA GTCATGTATT    881
Asn Leu Asp Cys Tyr Ser Gln Arg Pro Phe Ala
        235                 240

AATCTTGGCC CTCCATAAAA TACAATAAGA GCATCGTCTC CTATCTACAT GCTGTAAGAT    941

GTAACTATGG TAACCTTTTA TGGGGAACAT AACAAAGGCA TCTCGTATAG ATGCTTTGCT   1001

A                                                                   1002
```

-continued (2) INFORMATION FOR SEQ ID NO:10:

(i) SEQUENCE CHARACTERISTICS:
(A) LENGTH: 266 amino acids
(B) TYPE: amino acid
(D) TOPOLOGY: linear (ii) MOLECULE TYPE: protein (xi) SEQUENCE DESCRIPTION: SEQ ID NO: 10:

```
Met Arg Ser Leu Ala Val Val Val Ala Val Val Ala Thr Val Ala Met
-23         -20                 -15                 -10

Ala Ile Gly Thr Ala Arg Gly Ser Val Ser Ser Ile Val Ser Arg Ala
        -5                  1               5

Gln Phe Asp Arg Met Leu Leu His Arg Asn Asp Gly Ala Cys Gln Ala
 10                  15                  20                  25

Lys Gly Phe Tyr Thr Tyr Asp Ala Phe Val Ala Ala Ala Ala Ala Phe
                 30                  35                  40

Pro Gly Phe Gly Thr Thr Gly Ser Ala Asp Ala Gln Lys Arg Glu Val
             45                  50                  55

Ala Ala Phe Leu Ala Gln Thr Ser His Glu Thr Thr Gly Gly Trp Ala
        60                  65                  70

Thr Ala Pro Asp Gly Ala Phe Ala Trp Gly Tyr Cys Phe Lys Gln Glu
    75                  80                  85

Arg Gly Ala Ser Ser Asp Tyr Cys Thr Pro Ser Ala Gln Trp Pro Cys
 90                  95                 100                 105

Ala Pro Gly Lys Arg Tyr Tyr Gly Arg Gly Pro Ile Gln Leu Ser His
                110                 115                 120

Asn Tyr Asn Tyr Gly Pro Ala Gly Arg Ala Ile Gly Val Asp Leu Leu
            125                 130                 135

Ala Asn Pro Asp Leu Val Ala Thr Asp Ala Thr Val Gly Phe Lys Thr
        140                 145                 150

Ala Ile Trp Phe Trp Met Thr Ala Gln Pro Pro Lys Pro Ser Ser His
    155                 160                 165

Ala Val Ile Ala Gly Gln Trp Ser Pro Ser Gly Ala Asp Arg Ala Ala
170                 175                 180                 185

Gly Arg Val Pro Gly Phe Gly Val Ile Thr Asn Ile Ile Asn Gly Gly
                190                 195                 200

Ile Glu Cys Gly His Gly Gln Asp Ser Arg Val Ala Asp Arg Ile Gly
            205                 210                 215

Phe Tyr Lys Arg Tyr Cys Asp Ile Leu Gly Val Gly Tyr Gly Asn Asn
        220                 225                 230

Leu Asp Cys Tyr Ser Gln Arg Pro Phe Ala
    235                 240
```

(2) INFORMATION FOR SEQ ID NO:11:

(i) SEQUENCE CHARACTERISTICS:
(A) LENGTH: 1235 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Hordeum vulgare
(B) STRAIN: L.

-continued

```
    (ix) FEATURE:
          (A) NAME/KEY: 5'UTR
          (B) LOCATION: 1..48

    (ix) FEATURE:
          (A) NAME/KEY: CDS
          (B) LOCATION: 49..1050
          (D) OTHER INFORMATION: /partial /codon_start= 49 /function=
              "glucanase" /product= "preprotein of the glucanase GluG"

    (ix) FEATURE:
          (A) NAME/KEY: 3'UTR
          (B) LOCATION: 1051..1235
          (D) OTHER INFORMATION: /partial /note= "14 nucleotides at the
              3'end not shown."

    (ix) FEATURE:
          (A) NAME/KEY: polyA_signal
          (B) LOCATION: 1083..1088
          (D) OTHER INFORMATION: /note= "potential polyadenylation
              signal"

    (ix) FEATURE:
          (A) NAME/KEY: polyA_signal
          (B) LOCATION: 1210..1215
          (D) OTHER INFORMATION: /note= "potential polyadenylation
              signal"

    (ix) FEATURE:
          (A) NAME/KEY: mat_peptide
          (B) LOCATION: 133..1050

    (xi) SEQUENCE DESCRIPTION: SEQ ID NO: 11:

GGCAGCATTG CATAGCATTT GAGCACCAGA TACTCCGTGT GTGCACCA ATG GCT AGA      57
                                                     Met Ala Arg
                                                     -28

AAA GAT GTT GCC TCC ATG TTT GCA GTT GCT CTC TTC ATT GGA GCA TTC      105
Lys Asp Val Ala Ser Met Phe Ala Val Ala Leu Phe Ile Gly Ala Phe
-25                 -20                 -15                 -10

GCT GCT GTT CCT ACG AGT GTG CAG TCC ATC GGC GTA TGC TAC GGC GTG      153
Ala Ala Val Pro Thr Ser Val Gln Ser Ile Gly Val Cys Tyr Gly Val
                -5                   1               5

ATC GGC AAC AAC CTC CCC TCC CGG AGC GAC GTG GTG CAG CTC TAC AGG      201
Ile Gly Asn Asn Leu Pro Ser Arg Ser Asp Val Val Gln Leu Tyr Arg
        10                  15                  20

TCC AAG GGC ATC AAC GGC ATG CGC ATC TAC TTC GCC GAC GGG CAG GCC      249
Ser Lys Gly Ile Asn Gly Met Arg Ile Tyr Phe Ala Asp Gly Gln Ala
    25                  30                  35

CTC TCG GCC GTC CGC AAC TCC GGC ATC GGC CTC ATC CTC GAC ATC GGC      297
Leu Ser Ala Val Arg Asn Ser Gly Ile Gly Leu Ile Leu Asp Ile Gly
 40                  45                  50                  55

AAC GAC CAG CTC GCC AAC ATC GCC GCC AGC ACC TCC AAC GCG GCC TCC      345
Asn Asp Gln Leu Ala Asn Ile Ala Ala Ser Thr Ser Asn Ala Ala Ser
                60                  65                  70

TGG GTC CAG AAC AAC GTG CGG CCC TAC TAC CCT GCC GTG AAC ATC AAG      393
Trp Val Gln Asn Asn Val Arg Pro Tyr Tyr Pro Ala Val Asn Ile Lys
            75                  80                  85

TAC ATC GCC GCC GGC AAC GAG GTG CAG GGC GGC GCC ACG CAG AGC ATC      441
Tyr Ile Ala Ala Gly Asn Glu Val Gln Gly Gly Ala Thr Gln Ser Ile
        90                  95                 100

CTG CCG GCC ATG CGC AAC CTC AAC GCG GCC CTC TCC GCG GCG GGG CTC      489
Leu Pro Ala Met Arg Asn Leu Asn Ala Ala Leu Ser Ala Ala Gly Leu
    105                 110                 115

GGC GCC ATC AAG GTG TCC ACC TCC ATC CGG TTC GAC GAG GTG GCC AAC      537
Gly Ala Ile Lys Val Ser Thr Ser Ile Arg Phe Asp Glu Val Ala Asn
120                 125                 130                 135
```

-continued

```
TCC TTC CCG CCC TCC GCC GGC GTG TTC AAG AAC GCC TAC ATG ACG GAC       585
Ser Phe Pro Pro Ser Ala Gly Val Phe Lys Asn Ala Tyr Met Thr Asp
            140                 145                 150

GTG GCC CGG CTC CTG GCG AGC ACC GGC GCG CCG CTG CTC GCC AAC GTC       633
Val Ala Arg Leu Leu Ala Ser Thr Gly Ala Pro Leu Leu Ala Asn Val
            155                 160                 165

TAC CCC TAC TTC GCG TAC CGT GAC AAC CCC GGG AGC ATC AGC CTG AAC       681
Tyr Pro Tyr Phe Ala Tyr Arg Asp Asn Pro Gly Ser Ile Ser Leu Asn
        170                 175                 180

TAC GCG ACG TTC CAG CCG GGC ACC ACC GTG CGT GAC CAG AAC AAC GGG       729
Tyr Ala Thr Phe Gln Pro Gly Thr Thr Val Arg Asp Gln Asn Asn Gly
    185                 190                 195

CTG ACC TAC ACG TCC CTG TTC GAC GCG ATG GTG GAC GCC GTG TAC GCG       777
Leu Thr Tyr Thr Ser Leu Phe Asp Ala Met Val Asp Ala Val Tyr Ala
200                 205                 210                 215

GCG CTG GAG AAG GCC GGC GCG CCG GCG GTG AAG GTG GTG GTG TCG GAG       825
Ala Leu Glu Lys Ala Gly Ala Pro Ala Val Lys Val Val Val Ser Glu
                220                 225                 230

AGC GGG TGG CCG TCG GCG GGC GGG TTT GCG GCG TCG GCC GGC AAT GCG       873
Ser Gly Trp Pro Ser Ala Gly Gly Phe Ala Ala Ser Ala Gly Asn Ala
            235                 240                 245

CGG ACG TAC AAC CAG GGG CTG ATC AAC CAC GTC GGC GGG GGC ACG CCC       921
Arg Thr Tyr Asn Gln Gly Leu Ile Asn His Val Gly Gly Gly Thr Pro
        250                 255                 260

AAG AAG CGG GAG GCG CTG GAG ACG TAC ATC TTC GCC ATG TTC AAC GAG       969
Lys Lys Arg Glu Ala Leu Glu Thr Tyr Ile Phe Ala Met Phe Asn Glu
    265                 270                 275

AAC CAG AAG ACC GGG GAC GCC ACG GAG AGG AGC TTC GGG CTC TTC AAC      1017
Asn Gln Lys Thr Gly Asp Ala Thr Glu Arg Ser Phe Gly Leu Phe Asn
280                 285                 290                 295

CCG GAC AAG TCG CCG GCA TAC AAC ATC CAG TTC TAGTACGTGT AGCTACCTAG   1070
Pro Asp Lys Ser Pro Ala Tyr Asn Ile Gln Phe
                300                 305

CTCACATACC TAAATAAATA AGCTGCACGT ACGTACGTAA TGCGGCATCC AAGTGTAACG   1130

TAGACACGTA CATTCATCCA TGGAAGAGTG CAACCAAGCA TGCGTTAACT TCCTGGTGAT   1190

GATACATCAT CATGGTATGA ATAAAAGATA TGGAAGATGT TATGA                   1235
```

(2) INFORMATION FOR SEQ ID NO: 12:

(i) SEQUENCE CHARACTERISTICS:
(A) LENGTH: 334 amino acids
(B) TYPE: amino acid
(D) TOPOLOGY: linear (ii) MOLECULE TYPE: protein (xi) SEQUENCE DESCRIPTION: SEQ ID NO: 12:

```
Met Ala Arg Lys Asp Val Ala Ser Met Phe Ala Val Ala Leu Phe Ile
-28         -25                 -20                 -15

Gly Ala Phe Ala Ala Val Pro Thr Ser Val Gln Ser Ile Gly Val Cys
        -10                 -5                   1

Tyr Gly Val Ile Gly Asn Asn Leu Pro Ser Arg Ser Asp Val Val Gln
  5                  10                  15                  20

Leu Tyr Arg Ser Lys Gly Ile Asn Gly Met Arg Ile Tyr Phe Ala Asp
                 25                  30                  35

Gly Gln Ala Leu Ser Ala Val Arg Asn Ser Gly Ile Gly Leu Ile Leu
            40                  45                  50

Asp Ile Gly Asn Asp Gln Leu Ala Asn Ile Ala Ala Ser Thr Ser Asn
        55                  60                  65
```

-continued

```
Ala Ala Ser Trp Val Gln Asn Asn Val Arg Pro Tyr Tyr Pro Ala Val
     70                  75                  80

Asn Ile Lys Tyr Ile Ala Ala Gly Asn Glu Val Gln Gly Gly Ala Thr
 85                  90                  95                 100

Gln Ser Ile Leu Pro Ala Met Arg Asn Leu Asn Ala Ala Leu Ser Ala
                105                 110                 115

Ala Gly Leu Gly Ala Ile Lys Val Ser Thr Ser Ile Arg Phe Asp Glu
            120                 125                 130

Val Ala Asn Ser Phe Pro Pro Ser Ala Gly Val Phe Lys Asn Ala Tyr
        135                 140                 145

Met Thr Asp Val Ala Arg Leu Leu Ala Ser Thr Gly Ala Pro Leu Leu
    150                 155                 160

Ala Asn Val Tyr Pro Tyr Phe Ala Tyr Arg Asp Asn Pro Gly Ser Ile
165                 170                 175                 180

Ser Leu Asn Tyr Ala Thr Phe Gln Pro Gly Thr Thr Val Arg Asp Gln
                185                 190                 195

Asn Asn Gly Leu Thr Tyr Thr Ser Leu Phe Asp Ala Met Val Asp Ala
            200                 205                 210

Val Tyr Ala Ala Leu Glu Lys Ala Gly Ala Pro Ala Val Lys Val Val
        215                 220                 225

Val Ser Glu Ser Gly Trp Pro Ser Ala Gly Gly Phe Ala Ala Ser Ala
    230                 235                 240

Gly Asn Ala Arg Thr Tyr Asn Gln Gly Leu Ile Asn His Val Gly Gly
245                 250                 255                 260

Gly Thr Pro Lys Lys Arg Glu Ala Leu Glu Thr Tyr Ile Phe Ala Met
                265                 270                 275

Phe Asn Glu Asn Gln Lys Thr Gly Asp Ala Thr Glu Arg Ser Phe Gly
            280                 285                 290

Leu Phe Asn Pro Asp Lys Ser Pro Ala Tyr Asn Ile Gln Phe
        295                 300                 305
```